United States Patent
Schneidmiller et al.

(10) Patent No.: US 8,394,358 B2
(45) Date of Patent: Mar. 12, 2013

(54) WASP, HORNET, AND YELLOWJACKET SPRAY REPELLANT AND NEST PESTICIDE

(75) Inventors: Rodney G. Schneidmiller, Greenacres, WA (US); Qing-He Zhang, Spokane Valley, WA (US); Guiji Zhou, Spokane Valley, WA (US); Doreen R. Hoover, Spokane, WA (US)

(73) Assignee: Sterling International Inc., Spokane, WA (US)

( * ) Notice: Subject to any disclaimer, the term of this patent is extended or adjusted under 35 U.S.C. 154(b) by 0 days.

(21) Appl. No.: 13/612,031

(22) Filed: Sep. 12, 2012

(65) Prior Publication Data

US 2013/0004603 A1 Jan. 3, 2013

Related U.S. Application Data

(62) Division of application No. 13/250,707, filed on Sep. 30, 2011.

(60) Provisional application No. 61/392,369, filed on Oct. 12, 2010.

(51) Int. Cl.
*A01N 25/02* (2006.01)

(52) U.S. Cl. ......................................................... 424/43

(58) Field of Classification Search ........................ None
See application file for complete search history.

(56) References Cited

U.S. PATENT DOCUMENTS

| | | |
|---|---|---|
| 5,573,770 A | 11/1996 | Kern |
| 6,548,085 B1 | 4/2003 | Zobitne |
| 7,393,528 B2 | 7/2008 | Tvedten |
| 2006/0165746 A1 | 7/2006 | Markus |
| 2007/0098750 A1 | 5/2007 | Bessette |
| 2007/0166342 A1 | 7/2007 | Darling |
| 2007/0178128 A1 | 8/2007 | Bessette |
| 2007/0190094 A1 | 8/2007 | Bessette |
| 2008/0095813 A1 | 4/2008 | Kiec |
| 2008/0107640 A1 | 5/2008 | Tvedten |
| 2008/0166415 A1* | 7/2008 | Markus et al. ................ 424/490 |
| 2008/0187607 A1 | 8/2008 | Bessette |
| 2009/0099135 A1 | 4/2009 | Enan |
| 2010/0144888 A1 | 6/2010 | Bessette |

OTHER PUBLICATIONS

International Search Report and Written Opinion mailed Apr. 24, 2012, issued in related International Application No. PCT/US2011/054338, filed Sep. 30, 2011, 6 pages.

\* cited by examiner

*Primary Examiner* — James H. Alstrum-Acevedo
*Assistant Examiner* — Monica Shin
(74) *Attorney, Agent, or Firm* — Christensen O'Connor Johnson Kindness PLLC

(57) ABSTRACT

Methods for killing insects and a nest are disclosed. The methods may be used to disrupt a colony of nest-dwelling insects. The insects may include wasps, hornets, and yellowjackets.

3 Claims, No Drawings

WASP, HORNET, AND YELLOWJACKET SPRAY REPELLANT AND NEST PESTICIDE

CROSS-REFERENCE TO RELATED APPLICATION

This application is a division of U.S. patent application Ser. No. 13/250,707, filed Sep. 30, 2011, which claims the benefit of U.S. Provisional Application No. 61/392,369, filed Oct. 12, 2010. Both applications are fully incorporated herein expressly by reference.

BACKGROUND

Conventional insecticides kill insects by coming in contact with the insect. Many insecticides work by interfering with the insect's nervous system, leading to death of the insect. Insecticides can fall into a number of broad, compound categories, including organochlorine compounds, organophosphates, carbamates, and pyrethrins. Many organochlorine insecticides have been banned in the U.S. due to their persistence in the environment and their carcinogenicity. The resistance to biodegradation may contribute to the accumulation of organochlorine toxins in humans by introduction into the food chain or through contamination of drinking water sources. Organophosphate and carbamate insecticides have largely replaced organochlorine insecticides. The toxicity to humans can vary significantly between the different compounds in these classes. Compared to organochlorine compounds, however, organophosphates and carbamates generally do not bioaccumulate and are less of a concern in the contamination of water. Organophosphates and carbamates, however, can be poisonous and have adverse health effects on humans either through inhalation, absorption through the skin or accidental ingestion. Pyrethrins are natural insecticides derived from species of *Chrysanthemum* plants. Their toxicity to humans may be considered less of a risk than organophosphates or carbamates. The search for even less toxic, effective insecticides has led to the development of "insecticides" that kill insects through nontoxic means, such as attracting the insects within a trap, where the insects die of starvation or through drowning in water. Nevertheless, even with the introduction of generally nontoxic means for killing insects, a need still exists for additional means or substances that may be used in the control of insects.

SUMMARY

In one embodiment, a method for killing insects with various development stages residing in a nest is disclosed. The method includes applying a composition on or in proximity to an active nest, wherein the composition is not only effective to kill insects through contact or fumigation but, even more importantly, also to repel insects (not directly contacted by/with the composition) bringing food to the nest for a sufficient period to kill the larvae, interrupt the trophallaxis activity of the adult insects, and destroy the nest. The compositions disclosed herein include natural compounds that are responsible for disrupting a colony of nest-dwelling insects, and killing the nest.

In one embodiment, the method may further include spraying the composition on the nest.

In one embodiment, the method may further include spraying the composition to interrupt and/or stop the alarm pheromone release or response of the adult insects and, therefore, reduce the aggressiveness of the stinging adults and, ultimately, reduce the risk of being stung.

In one embodiment, the composition includes an essential oil.

In one embodiment, the composition includes an essential oil selected from the group consisting of anise oil, castor oil, cedar oil, cinnamon oil, citronella oil, clove oil, corn oil, cottonseed oil, fennel seed oil, garlic oil, geranium oil, lavender oil, lemongrass oil, linseed oil, mint oil, patchouli oil, pennyroyal oil, peppermint oil, Roman chamomile oil, rosemary oil, sage oil, sesame oil, soybean oil, spearmint oil, thyme oil, wintergreen oil, and ylang ylang oil, or any combination thereof.

In one embodiment, the composition includes a compound selected from the group consisting of l-menthone, P-menthone, eugenol, E-citral, Z-citral, pulegone, α-thujone, β-thujone, methyl benzoate, d-carvone, methyl salicylate, E/Z-nepetalactone, Z/E-nepetalactone, 3-octanol, benzyl acetate, and citronellal, or any combination thereof.

In one embodiment, the composition comprises at least one of lemongrass oil and clove oil.

In one embodiment, the composition comprises lemongrass oil and clove.

In one embodiment, the composition comprises lemongrass oil, clove oil, mineral oil, isopropyl alcohol, and isopropyl myristate.

In one embodiment, the composition comprises lemongrass oil, clove oil, rosemary oil and geranium oil.

In one embodiment, the composition comprises lemongrass oil, clove oil, geranium oil and mineral oil, isopropyl alcohol, and isopropyl myristate.

In one embodiment, the composition comprises lemongrass oil, clove oil, rosemary oil, geranium oil and mineral oil, isopropyl alcohol, and isopropyl myristate.

In one embodiment, the composition further includes a propellant, including carbon dioxide, nitrous oxide, hydrocarbons, propane, n-butane, isobutane, or any hydrofluoroalkane.

In one embodiment, the method further includes applying the composition to the inside of the nest via the entrance hole(s), especially to the underground nests.

In one embodiment, the method includes applying the composition to an aerial nest or ground nest.

In one embodiment, the method further includes applying the composition to the inside of open cells which comprise the nest.

In one embodiment, the method further includes applying the composition to the outside of the aerial nest with live insects.

In one embodiment, the insects are the larvae, pupae or adults of wasps, yellowjackets, or hornets.

In another embodiment, a method for disrupting a nest-dwelling colony of insects is disclosed. The method includes applying a composition on or inside or in proximity to a nest; and with the composition, repelling insects from the nest for an effective period to cause the insects to abandon the nest, wherein the composition comprises lemongrass oil and clove oil. The method includes repelling insects from the nest and particularly the insects that have not been contacted by or with the composition. The composition may further include rosemary oil, geranium oil, a carrier, a propellant gas, isopropyl alcohol, isopropyl myristate, and mineral oil. Unlike other methods or compositions, the methods and compositions disclosed herein have the advantage that they do not need to be applied directly on the insects to be effective in disrupting an entire colony.

The disclosed method provides an effective multiple functional/modality (both insecticidal and non-toxic) means for controlling insects that relies on natural substances to not only kill or fumigate but also disrupt or block the olfactory system and further interrupt the life cycle of insects by depriving larvae of food by repelling the adult insects from the nest. As a result, the larvae in the nests fail to mature into adult insects.

DETAILED DESCRIPTION

During the autumn and winter months, many insect colonies die off, leaving only the mated queens, which must then leave the nest and find a suitable habitat to hibernate for the winter. After winter, the queens will emerge from hibernation to start a new colony. The life cycle of a typical nesting insect will begin with the queen building a nest. The queen gathers cellulose materials in the environment, such as bark, dead grass, etc. The queen mixes the materials with saliva and uses the mixture to start forming the nest. A nest will typically have cells in which the queen will lay her first eggs. The eggs hatch into larvae, which the queen will nurture and feed until the larvae develop into worker insects. The worker insects will continue building the nest while the queen continues to lay eggs. The worker insects will also gather food for the queen and the developing larvae. Eventually, the nest may grow to include hundreds of cells with each one potentially having an egg or a larva. The larvae need food to grow into adult insects. Adult insects bring the food to the larvae. Larvae in return secrete a sugar material relished by the adults in a trophallaxis fashion.

The present disclosure is related to a method of killing insects (both larvae and adults) in the nest without the use of toxic chemicals. A composition is disclosed that uses natural substances as actives for disrupting a colony of nest-dwelling insects. The method of using the composition does not rely on, and indeed it is not necessary for, the composition to be applied directly on insects to be effective. The composition may be applied on or in proximity of a nest. The composition is effective in repelling insects from the nest, thereby killing immature larvae in the nest. Additionally, insects that do happen to be contacted by the composition may be knocked down and killed quickly due to suffocation.

In one embodiment, a method for killing insects is based on the principle that larvae in the nest are vulnerable during this early period in their life cycle since they depend on worker insects to bring food to the nest. The disclosed method is effective in killing the larvae in the nest. The feeding cycle of larvae can be disrupted by applying a dose of a composition on or inside the nest or in the immediate proximity of the nest. The compositions disclosed herein are effective to repel the adult insects (mostly workers) bringing food to the nest. As a result, the insect larvae will die from lack of food. The composition may be applied directly on or inside the nest or in the proximity to the nest. The composition may be applied in sufficient quantities to saturate the nest. The composition may be applied on the inside of the cells if they are open or on the outside of the cells if they are closed. One application may suffice to repel the insects for a sufficient period of time to kill the larvae and the colony. However, in other embodiments, the composition may be applied multiple times over an extended period of time.

In one embodiment, a composition is used in the disruption of the growth of the larvae, effectively killing the larvae and the nest with the use of natural chemicals in a non-toxic mode of action. While it may not be possible to directly apply the composition to the larvae, nonetheless, the larvae are killed indirectly through starvation when the adults are repelled from the nest. The same composition is useful in also knocking down and killing insects that are directly contacted with the composition. The killing of the larvae through the application of natural substances that repel adult insects from the nest provides a non-toxic and effective means of controlling insects. The composition is also effective in disrupting and/or deterring the feeding activity and/or life cycle of the adult workers. Adult insects, similar to larvae, feed at the nest. Accordingly, the method in accordance with one embodiment of the invention is effective in also disrupting and/or deterring the feeding activity of the adult worker insects. Additionally, the queen in the nest is also deprived of food that would normally be brought by the worker adult insects. The feeding activity of the queen insect is likewise disrupted and/or deterred in accordance with one embodiment of the invention. Because neither the queen nor the adult workers feed, this can negatively affect the overall activity of the nest, thus resulting in fewer insects and eventually the nest will die off.

A further benefit is the added safety when applying the disclosed composition. When applied on or in proximity to the nest, the composition acts as a repellent to deter insects from returning to the nest. However, during the application process, a concern with many pesticides is the aggressive reaction that is evoked in the stinging insects caused by the release of alarm pheromones. The disclosed composition is beneficial in that it strongly diminishes the aggressive behavior of the insects by stopping or interrupting alarm pheromone release or response, or both. Such volatile repellent composition may even block the olfactory (sensory) system of the adult insects. Accordingly, the composition may reduce the risk of being stung by the insects during the spray application.

The compositions that may be used in the methods disclosed herein include one or more essential oils or their constituent compounds. The essential oils and their constituent compounds are derived from plants and other sources found in nature. The compositions are also meant to include synthetically manufactured compounds as long as the chemical structure and formulations are identical or substantially similar to the compound found in nature. The composition may also include inerts, such as carriers, surfactants, and propellants.

In one embodiment, the composition includes essential oils as the active ingredients. The essential oil(s) may be selected from the group consisting of anise oil, castor oil, cedar oil, cinnamon oil, citronella oil, clove oil, corn oil, cottonseed oil, fennel seed oil, garlic oil, geranium oil, lavender oil, lemongrass oil, linseed oil, mint oil, patchouli oil, pennyroyal oil, peppermint oil, Roman chamomile oil, rosemary oil, sage oil, sesame oil, soybean oil, spearmint oil, thyme oil, wintergreen oil, and ylang ylang oil, or any combination thereof.

Each of the essential oils above may include hundreds of compounds. The active compounds identified as repellents in one or more of the above list of essential oils may also be used in the compositions disclosed herein. The active compounds include, but are not limited to, the compounds selected from the group consisting of I-menthone, P-menthone, eugenol, E-citral, Z-citral, pulegone, α-thujone, β-thujone, methyl benzoate, d-carvone, methyl salicylate, E/Z-nepetalactone, Z/E-nepetalactone, 3-octanol, benzyl acetate, citronellal, or any combination thereof. The compositions may include anyone of the compounds found in the above-referenced essential oils in an isolated form together with essential oils. For example, an isolated compound can be combined with one or more essential oils. An isolated compound refers to a compound that has been separated from an essential oil or synthesized independently without extracting the compound from an essential oil. An isolated compound may be a purified compound. However, it is to be understood that depending on the purification method, trace compounds may still be present.

The compositions can be delivered through various means including an aerosolized spray, powder, or liquid. When used in a spray, a propellant may optionally be included. The propellant can include, but is not limited to, nitrogen, carbon dioxide, nitrous oxide, hydrocarbons, such as propane, n-butane, isobutane, and hydrofluoroalkanes. In the spray embodiments disclosed herein, any one or more of the propellants may be included. Other spray means can use spray mechanisms, such as pump or trigger sprayers, and other manually activated pump mechanisms.

In one embodiment, a composition includes lemongrass oil, clove oil, isopropyl alcohol, isopropyl myristate, mineral oil, and optionally a propellant, such as carbon dioxide or nitrogen.

Lemongrass oil is extracted from one of numerous species of grasses belonging to the genus *Cymbopogon*. Clove oil is extracted from the tree species *Syzygium aromaticum*. Isopropyl alcohol is used as a solvent for the oils in the composition. Other alcohols and solvents besides isopropyl alcohol may be used. Isopropyl myristate is a surfactant. Mineral oil is a carrier.

In one embodiment, the lemongrass oil in the composition includes from 1% by weight to 2.5% by weight based on the total weight of the composition. In one embodiment, the concentration of clove oil in the composition includes from 1% by weight to 2.5% by weight based on the total weight of the composition. In one embodiment, the concentration of isopropyl alcohol in the composition includes from 10% by weight to 30% by weight, preferably 20% by weight, all based on the total weight of the composition. In another embodiment, isopropyl alcohol can be omitted from the composition. In one embodiment, the concentration of isopropyl myristate includes from 16% by weight to 40% by weight based on the total weight of the composition. However, in another embodiment, the isopropyl myristate can be omitted from the composition. In one embodiment, the mineral oil concentration in the composition includes from 31.5% by weight to 91.5% by weight based on the total weight of the composition. In one embodiment, the concentration of carbon dioxide propellant in the composition is approximately 3.5% by weight. In one embodiment, rosemary oil may be used with lemongrass oil and clove oil. In one embodiment, geranium oil may be used with lemongrass oil and clove oil.

In one embodiment, the composition includes about 2.5% lemongrass oil, about 2.5% clove oil, about 20% isopropyl alcohol, about 40% isopropyl myristate, about 31.5% mineral oil, and optionally a propellant, such as about 3.5% carbon dioxide or nitrogen. All percents are weight percents based on the total weight of the composition.

In one embodiment, the composition includes about 2.5% lemongrass oil, about 2.5% clove oil, about 91.5% mineral oil, and optionally a propellant, such as about 3.5% carbon dioxide or nitrogen. All percents are weight percents based on the total weight of the composition.

In one embodiment, the composition includes about 1% lemongrass oil, about 1% clove oil, about 20% isopropyl alcohol, about 16% isopropyl myristate, about 58.5% mineral oil, and optionally a propellant, such as about 3.5% carbon dioxide or nitrogen. All percents are weight percents based on the total weight of the composition.

In one embodiment, the composition includes about 2% lemongrass oil, about 2% clove oil, about 20% isopropyl alcohol, about 16% isopropyl myristate, about 56.5% mineral oil, and, optionally, a propellant, such as about 3.5% carbon dioxide or nitrogen. All percents are weight percents based on the total weight of the composition.

In one embodiment, the composition includes about 1.5% lemongrass oil, about 1.5% clove oil, about 1% geranium oil, about 20% isopropyl alcohol, about 16% isopropyl myristate, about 56.5% mineral oil, and, optionally, a propellant, such as about 3.5% carbon dioxide or nitrogen. All percents are weight percents based on the total weight of the composition.

In one embodiment, the composition includes about 1.5% lemongrass oil, about 1.5% clove oil, about 1% rosemary oil, about 20% isopropyl alcohol, about 16% isopropyl myristate, about 56.5% mineral oil, and, optionally, a propellant, such as about 3.5% carbon dioxide or nitrogen. All percents are weight percents based on the total weight of the composition.

In one embodiment, the composition includes about 1% lemongrass oil, about 1% clove oil, about 1% geranium oil, about 1% rosemary oil, about 20% isopropyl alcohol, about 16% isopropyl myristate, about 56.5% mineral oil, and optionally a propellant, such as about 3.5% carbon dioxide or nitrogen. All percents are weight percents based on the total weight of the composition.

In one embodiment, the composition includes about 1.99% lemongrass oil, about 1.99% clove oil, about 0.01% geranium oil, about 0.01% rosemary oil, about 20% isopropyl alcohol, about 16% isopropyl myristate, about 56.5% mineral oil, and, optionally, a propellant, such as about 3.5% carbon dioxide or nitrogen.

In one embodiment, the composition includes about 2% lemongrass oil, about 2% clove oil, about 0.01% geranium oil, about 0.01% rosemary oil, about 20% isopropyl alcohol, about 16% isopropyl myristate, about 56.5% mineral oil, and, optionally, a propellant, such as about 3.5% carbon dioxide or nitrogen.

In one embodiment, the compositions may be used on any nest-dwelling insects or for disrupting a nest-dwelling colony of insects. In one embodiment, the insects may be from the order Hymenoptera and specifically from the family Vespidae, commonly referred to as paper wasps, yellowjackets, and hornets.

In some embodiments, an insect is selected from the group consisting of paper wasps, yellowjackets, and hornets, or any combination thereof. Representative examples of insects that are repelled or killed by the compositions include *Polistes annularis; P. apaches; P. aurifer* (Golden Paper Wasp); *P. bellicosus; P. carolina; P. dominula* (European Paper Wasp); *P. dorsalis; P. exclamans; P. fuscatus; P. metricus; P. perplexus*); *Vespula acadica* Sladen; *V. atropilosa* Sladen (Prairie Yellowjacket); *V. austriaca* Panzer; *V. consobrina* Saussure (Blackjacket); *V. flavopilosa* Jakobson (Transition Yellowjacket); *V. germanica* Fabricius (German Yellowjacket); *V. maculifrons* Buysson (Eastern Yellowjacket); *V. pensylvanica* Saussure (Western Yellowjacket); *V. squamosa* Drury (Southern Yellowjacket); *V. sulphurea* Saussure (California Yellowjacket); *V. vidua* Saussure (Forest Yellowjacket); *V. vulgaris* Linnaeus (Common Yellowjacket); *Dolichovespula arenaria* Fabricius (Aerial Yellowjackets); *D. maculata* Linnaeus (Bald-faced Hornet); *D. norvegicoides* Sladen (Arctic Yellowjacket); *Vespa crabro* Linnaeus (European Hornet); *V. mandarinia* Smith (Asian Giant Hornet); and *V. orientalis* Linnaeus (Oriental Hornet). Any combination of these insects is contemplated.

In one embodiment, any one or more of the essential oils and compounds can be combined to repel any insect species. In another embodiment, any one or more of the essential oils and compounds can be combined to repel a single insect species selected from any insect species belonging to the order Hymenoptera. In another embodiment, any one or more of the essential oils and compounds can be combined to repel a limited group of insect species belonging to the order Hymenoptera. In another embodiment, any one or more of the essential oils and compounds can be combined to repel a single insect species selected from the family Vespidae. In another embodiment, any one or more of the essential oils and compounds can be combined to repel a limited group of insect species belonging to the family Vespidae. In another embodiment, any one or more of the essential oils and compounds can be combined to repel a single insect species belonging to the family Vespidae. In another embodiment, any one or more of the essential oils and compounds can be combined to repel a single insect species selected from any insect species belonging to the subfamily Polistinae. In another embodiment, any one or more of the essential oils and compounds can be combined to repel a limited group of insect species belonging to the subfamily Polistinae. In another embodiment, the essential oils and compounds can be combined to repel the group of insects, including wasps, yellowjackets, and hornets. In the above embodiments, any one or more of the essential oils and compounds can be combined to repel a targeted species of insect or a limited group of insect species, while not repelling other species outside the target. While the mention of certain insect orders and families are disclosed as being repelled or killed by the essential oils and compounds disclosed herein, it should not be construed to limit the present invention to repelling insects from any particular order or family, since the claims will define the scope of the invention. Accordingly, the compositions may be used to repel or kill any insect.

While the ability to disrupt a colony of nest-dwelling insects is a characteristic of the compositions, the compositions may also be used to directly kill insects. The compositions may effectively suffocate insects by coating them with the composition, such that the insect is immobilized and can be dead within seconds or minutes. Accordingly, in one embodiment, the composition is an insecticidal composition. The composition is effective to kill any insects that are directly contacted with the composition. The composition may suffocate the insects that are coated with the composition.

The disclosed compositions, including essential oils, may be used in various insect control methods. In one embodiment, the composition may be sprayed on or in proximity to the nest. In such case, the composition may immediately knockdown and subsequently kill the insects that were directly contacted by the composition. The composition is readily absorbed by the nest material so that the composition persists in the nest, and renders the nest unattractive to any insects attempting to return to the nest. The duration of the composition as an effective repellent can be greater than 1 day. However, the repellency effect depends on the amount of any one application. Applications may be repeated daily, or when a greater number of insects are seen around the nest after an initial application. At some point, by continuing the repellency effect, the insects will not return to the nest, effectively killing the nest and disrupting the colony.

EXAMPLES

Example 1

Laboratory Efficacy Tests

Four composition formulations (A, B, C, D in Table 1 below) were tested in lab cup bioassay trials on different social wasp species against a deionized (DI) water control.

TABLE 1

WHY spray formulations tested in lab cup bioassays

| | | Formulations (% by Wt) | | | |
|---|---|---|---|---|---|
| CAS # | Composition | A | B | C | D |
| 8007-02-1 | Lemongrass Oil | 2.5 | 2 | 1 | 2 |
| 8015-97-2 | Clove Oil | 2.5 | 2 | 1 | 2 |
| 8000-25-7 | Rosemary Oil | 0 | 0 | 1 | 0.01 |
| 8016-45-3 | Geranium Oil | 0 | 0 | 1 | 0.01 |
| 67-63-0 | Isopropyl Alcohol | 20 | 20 | 20 | 20 |
| 110-27-0 | Isopropyl Myristate | 40 | 16 | 16 | 16 |
| 8042-47-5 | Mineral oil | 31.5 | 56.5 | 56.5 | 56.5 |
| | CO2 or N2 Propellant | 3.5 | 3.5 | 3.5 | 3.5 |
| Sum | | 100 | 100 | 100 | 100 |

All the lab tests were conducted at Sterling International, Inc. in Spokane Valley, Wash. Each test required the placement of live insects inside plastic disposable cups (size 9 OZ=266 ml). The cups were covered with a mesh netting material via rubber band and suspended in a manner about 5 feet from the ground using a clear acrylic panel with holes cut approximately 27 cm apart into it to hold 3 cups on their side. There were 10 live insects placed into each cup which equaled a total of 30 insects tested for each formulation treatment or DI water control. From approximately 1 meter away, the testing scientist sprayed the cup 5 times trying to coat the entire cup with spray using a trigger spray bottle for DI water or pressurized can for treatment. Then, while timing, another scientist would observe and record the knockdown (falling to the "ground" or immobilized) and mortality effect of the sprays tested at 30 seconds, 1 minute, 3 minutes, 5 minutes, and 10 minutes. Each spray would be replicated on the three cups at the same time with the same species of insects. The tested insects and cups would then be discarded after the spray was tested and new cups with new insects would be tested on the next spray formulation or DI water control. The acrylic panels were also washed off thoroughly between treatments so there would be no cross contamination between treatments.

TABLE 2

Mean % (n = 3) of knockdown and mortality of social wasps after sprayed with different formulations of WHY sprays and DI water control

| | | % (at 30 sec) | | % at 1 min | | % at 3 min | | % at 5 min | | % at 10 min | |
|---|---|---|---|---|---|---|---|---|---|---|---|
| Social wasp species | Sprays | Knock down | Mortality | Knock down | Mortality | Knock down | Mortality | Knock down | Mortality | Knock down | Mortality |
| Dolichovespula maculata (Baldfaced hornet) | A | 100 | 0 | 100 | 13 | 100 | 97 | 100 | 100 | 100 | 100 |
| | B | 100 | 0 | 100 | 29 | 100 | 100 | 100 | 100 | 100 | 100 |
| | DI water | 0 | 0 | 0 | 0 | 0 | 0 | 0 | 0 | 0 | 0 |

TABLE 2-continued

Mean % (n = 3) of knockdown and mortality of social wasps after sprayed with different formulations of WHY sprays and DI water control

| Social wasp species | Sprays | % (at 30 sec) | | % at 1 min | | % at 3 min | | % at 5 min | | % at 10 min | |
|---|---|---|---|---|---|---|---|---|---|---|---|
| | | Knock down | Mortality | Knock down | Mortality | Knock down | Mortality | Knock down | Mortality | Knock down | Mortality |
| *Vespula* | B | 96 | 0 | 100 | 41 | 100 | 89 | 100 | 100 | 100 | 100 |
| *germanica* | C | 60 | 0 | 97 | 53 | 100 | 90 | 100 | 97 | 100 | 100 |
| (German yellowjacket) | DI water | 0 | 0 | 0 | 0 | 0 | 0 | 0 | 0 | 0 | 0 |
| *Polistes* | D | 100 | 100 | 100 | 100 | 100 | 100 | 100 | 100 | 100 | 100 |
| *dominulus* (European paper wasp) | DI water | 0 | 0 | 0 | 0 | 0 | 0 | 0 | 0 | 0 | 0 |
| *Dolichovespula* | D | 100 | 100 | 100 | 100 | 100 | 100 | 100 | 100 | 100 | 100 |
| *arenaria* (Aerial yellowjacket) | DI water | 0 | 0 | 0 | 0 | 0 | 0 | 0 | 0 | 0 | 0 |

In the lab tests, all the DI water controls showed zero knockdown or mortality effect on all the tested yellowjacket and paper wasp species during the 10 minute testing periods (Table 2). However, spray formulations A, B and C resulted in 60-100% knockdowns within 30 sec., and killed 97-100% of tested social wasps within 5 min, and obtained 100% mortality within 10 min. Interestingly, the spray formulation D was able to knock down and kill all the tested paper wasps and yellowjackets within 30 sec.

Example 2

Field Spray Tests on Live Baldfaced Hornet (*Dolichovespula maculata*) Nests

Three live Baldfaced hornet nests were tested with formulations A and B sprays in 2010.

Nest #1:

At approximately 11:00 am on Aug. 17, 2010, an active, football-size baldfaced hornet nest was sprayed with one can of the spray formulation A (see Table 1 for details) in Millvale, Wash. It was sprayed until there were no more *D. maculata* leaving the nest or not very much activity around the nest. This nest was left alone until approximately 5:00 pm on the same day when it was observed for activity. There was no activity of hornets leaving and little activity of hornets returning to the nest. A few *D. maculata* that were foraging earlier that day when the nest was sprayed were observed trying to return to the nest. These returning baldfaced hornets would get approximately a few inches away from the nest, but fly away never to land on the nest being repelled away by the spray. On Aug. 18, 2010, the nest was observed at approximately 4:20 pm. The nest had the same observations as the prior day when it was checked. There were no baldfaced hornets returning or leaving the nest. They would not land on the nest showing repellency to the spray though a few were still flying around in the vicinity of the nest. It was observed that a few of these foragers were congregating in a tree not far from the nest. The observations showed the nest was killed due to no activity of hornets seen leaving or returning. It was also concluded that the formulation A spray showed a repellency effect to the nest for >29 hours.

Nest #2:

At approximately 8:30 pm on Aug. 25, 2010, an active, football-size baldfaced hornet nest was sprayed with a can of the spray formulation B (see Table 1 for details) in Spokane, Wash. It was sprayed until there were no more *D. maculata* leaving the nest and very little activity from returning baldfaced hornets around the nest. It was observed that the baldfaced hornets would not land on the nest after it was sprayed with the formulation B. The nest was removed after it was killed and cut open to count the *D. maculata* present inside that were killed; the number of cells inside the nest (maximum size); the larvae remaining at this time of year; and the pupae remaining at this time of year. This nest had three tiers on the inside. There were 286 *D. maculata* adults killed inside the nest with only 9 barely alive ones that would not have survived because of the entrance hole being blocked by the dead spray-covered baldfaced hornets. The nest consisted of a total of 1738 cells of which there were 990 empty, 258 larvae, and 490 pupae. The observations showed the nest was killed with no activity of hornets leaving and very few baldfaced hornets trying to return and without landing or entering the nest. The repellency effect was observed as the nest was being sprayed and shortly after while removing the nest.

Nest #3:

At approximately 10:00 am on Sep. 10, 2010, an active, basketball-size baldfaced hornet nest was sprayed with the spray formulation B in Spokane Valley, Wash. It was sprayed until there were no more *D. maculata* leaving the nest and little activity of returning hornets to the nest. It was observed that the baldfaced hornets would not land on the nest after it was sprayed with the formulation. The nest was removed after it was killed and cut open for observations of the inside. The nest contained four tiers. There were 164 *D. maculata* adults killed inside the nest, which consisted of 21 females and 143 males. The nest contained of an estimated total of 2565 cells of which approximately 2458 were empty, 20 were larvae, and 87 were pupae. The observations showed the nest was killed with no activity of hornets leaving and very few baldfaced hornets returning to the nest. The insects that did return were not landing or entering the nest. The repellency effect was noted as the nest was being sprayed and shortly after it was sprayed while conducting the removal from its location.

While illustrative embodiments have been illustrated and described, it will be appreciated that various changes can be made therein without departing from the spirit and scope of the invention.

The embodiments of the invention in which an exclusive property or privilege is claimed are defined as follows:

1. An insecticidal composition, consisting essentially of:
about 2% by weight lemongrass oil;

about 2% by weight clove oil;
about 0.01% by weight rosemary oil; and
about 0.01% by weight geranium oil.

2. An insecticidal composition, comprising:
about 2% by weight lemongrass oil;
about 2% by weight clove oil;
about 0.01% by weight rosemary oil; and
about 0.01% by weight geranium oil.

3. The composition of claim 2, further comprising isopropyl alcohol, isopropyl myristate, mineral oil, and nitrogen.

* * * * *